United States Patent [19]
King et al.

[11] Patent Number: 5,827,871
[45] Date of Patent: Oct. 27, 1998

[54] MEDICAMENTS 1,2,3,4-TETRAHYDROCARBAZOLES AND 5-HT₁ AGONIST USE THEREOF

[75] Inventors: Francis David King; Laramie Mary Gaster, both of Harlow; Alberto Julio Kaumann, Trumpington; Rodney Christopher Young, Hertford, all of England

[73] Assignee: Smithkline Beecham plc, England

[21] Appl. No.: 442,720

[22] Filed: May 17, 1995

Related U.S. Application Data

[63] Continuation-in-part of Ser. No. 167,846, filed as PCT/GB92/01082, Jun. 17, 1992, Pat. No. 5,464,864.

[30] Foreign Application Priority Data

Jun. 26, 1991 [GB] United Kingdom .................. 9113802

[51] Int. Cl.⁶ ...................... A61K 31/40; C07D 209/82
[52] U.S. Cl. .................. 514/411; 514/212; 514/323; 540/602; 546/200; 548/448; 548/449
[58] Field of Search ................... 514/411, 212, 514/323; 540/602; 546/200; 548/448, 440, 449

[56] References Cited

FOREIGN PATENT DOCUMENTS 0 242 518  10/1997  European Pat. Off. .

Primary Examiner—Jacqueline Haley
Attorney, Agent, or Firm—Nora Stein-Fernandez; Janice E. Williams

[57] ABSTRACT

Use of a compound of general formula (I):

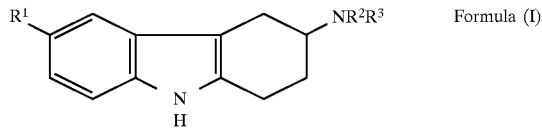

Formula (I)

wherein

R¹ represents hydrogen, halogen, trifluoromethyl, nitro, hydroxy, $C_{1-6}$alkyl, $C_{1-6}$alkoxy, aryl$C_{1-6}$alkoxy, $-CO_2R^4$, $-(CH_2)_nCN$, $-(CH_2)_nCONR^5R^6$, $-(CH_2)_nSO_2NR^5R^6$, $C_{1-6}$alkanoylamino$(CH_2)_n$, or $C_{1-6}$alkylsulphonylamino$(CH_2)_n$;

R⁴ represents hydrogen, $C_{1-6}$alkyl or aryl$C_{1-6}$alkyl;

R⁵ and R⁶ each independently represent hydrogen or $C_{1-6}$alkyl, or R⁵ and R⁶ together with the nitrogen atom to which they are attached form a ring;

n represents 0, 1 or 2; and

R² and R³ each independently represent hydrogen, $C_{1-6}$alkyl or benzyl or together with the nitrogen atom to which they are attached form a pyrrolidino, piperidino or hexahydroazepino ring;

or a physiologically acceptable salt thereof, in the manufacture of a medicament for the treatment of a condition where a 5-HT₁-like agonist is indicated, for example migraine. Novel compounds of formula (I), processes for preparing them and pharmaceutical compositions containing them are also described.

17 Claims, No Drawings

MEDICAMENTS 1,2,3,4-TETRAHYDROCARBAZOLES AND 5-HT₁ AGONIST USE THEREOF

This is a continuation-in-part application of application Ser. No. 08/167,846, filed Dec. 23, 1993, now U.S. Pat. No. 5,464,864, which is a U.S. national phase application of PCT/GB92/01082, filed Jun. 17, 1992, claiming priority from GB 9113802, filed Jun. 26, 1991.

The present invention relates to certain tetrahydrocarbazole derivatives for use in the treatment of disorders characterised by excessive vasodilatation, in particular the treatment of migraine.

Migraine is a non-lethal disease which has been reported to be suffered by one in ten individuals. The main symptom is headache; other symptoms include vomiting and photophobia. Currently, the most widely used treatment for migraine involves administration of ergotamine, dihydroergotamine or methysergide, which are also used prophylactically. These drugs are inter alia agonists of 5HT$_1$-like receptors but also have other actions; treatment with them is associated with a number of adverse side effects. In addition, some patients experience a "withdrawal headache" following the cessation of treatment with an ergot product, such as ergotamine, causing them to repeat the treatment and resulting in a form of addiction. More recently various tryptamine derivatives have been proposed for potential use in treating migraine.

In view of the foregoing, there is clearly a need for the provision of effective and safe medicaments for the treatment of migraine.

U.S. Pat. Nos. 4,257,952, 4,172,834, 4,062,864 and 3,959,309 disclose a broad class of tetrahydrocarbazoles of the formula:

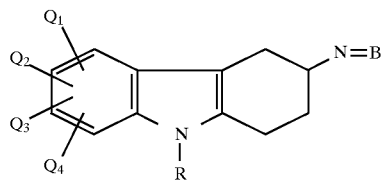

wherein N=B is inter alia —NHR' or —NR'R" where R' and R" are lower alkyl, aryl-lower alkyl or together form a heterocyclic ring; R is inter alia hydrogen; $Q_1$ is inter alia hydrogen, halogen, lower alkoxy, cyano, —CO$_2$R$_1$ or —CONR$_2$R$_3$ (where R$_1$ may be hydrogen, lower alkyl or —CH$_2$Ar and R$_2$ and R$_3$ are hydrogen, lower alkyl or together form a heterocyclic ring); $Q_2$ is inter alia hydrogen, aryl-(lower alkoxy), hydroxy, trihalomethyl, nitro or alkanoylamino, and $Q_3$ and $Q_4$ may each be inter alia hydrogen. These compounds are said to have analgesic, psychotropic and anthistaminic activities.

It has now surprisingly been found that certain tetrahydrocarbazoles are agonists and partial agonists at 5HT$_1$-like receptors and are expected to have utility in the treatment of conditions wherein a 5-HT$_1$-like agonist or partial agonist is indicated, in particular conditions associated with cephalic pain such as migraine, cluster headache and headache associated with vascular disorders. In this specification the term '5-HT$_1$-like agonist' will hereinafter be used to include partial agonists at this receptor.

The present invention therefore provides the use of compounds of general formula (I):

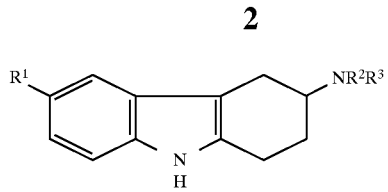

wherein:
R$^1$ represents hydrogen, halogen, trifluoromethyl, nitro, hydroxy, C$_{1-6}$alkyl, C$_{1-6}$alkoxy, arylC$_{1-6}$alkoxy, —CO$_2$R$^4$, —(CH$_2$)$_n$CN, —(CH$_2$)$_n$CONR$^5$R$^6$, —(CH$_2$)$_n$SO$_2$NR$^5$R$^6$, C$_{1-6}$alkanoylamino(CH$_2$)$_n$, or C$_{1-6}$alkylsulphonylamino(CH$_2$)$_n$;
R$^4$ represents hydrogen, C$_{1-6}$alkyl or arylC$_{1-6}$alkyl;
R$^5$ and R$^6$ each independently represent hydrogen or C$_{1-6}$alkyl, or R$^5$ and R$^6$ together with the nitrogen atom to which they are attached form a ring;
n represents 0, 1 or 2; and
R$^2$ and R$^3$ each independently represent hydrogen, C$_{1-6}$alkyl or benzyl or together with the nitrogen atom to which they are attached form a pyrrolidino, piperidino or hexahydroazepino ring;
and physiologically acceptable salts thereof, in the manufacture of a medicament for the treatment of a condition where a 5-HT$_1$-like agonist is indicated, in particular the treatment or prophylaxis of migraine.

The invention also provides a method of treatment of a condition wherein a 5-HT$_1$-like agonist is indicated, in particular migraine, which comprises administering to a subject in need thereof an effective amount of a compound of formula (I) or a physiologically acceptable salt thereof.

Suitably R$^1$ represents hydrogen, halogen, cyano, hydroxy, C$_{1-6}$alkoxy, arylC$_{1-6}$alkoxy, —CO$_2$R$^4$, —(CH$_2$)$_n$CONR$^5$R$^6$ or —(CH$_2$)$_n$SO$_2$NR$^5$R$^6$; and R$^2$ and R$^3$ each independently represent hydrogen or C$_{1-6}$alkyl.

It will be appreciated that compounds of formula (I) may contain one or more assymetric centres, and such compounds will exist as optical isomers (enantiomers). The invention thus includes all such enantiomers and mixtures, including racemic mixtures, thereof.

In the compounds of formula (I) a halogen atom may be a fluorine, chlorine, bromine or iodine atom. An alkyl group or moiety may have a straight or branched chain. Suitable aryl groups include for example unsaturated monocyclic or bicyclic rings and partially saturated bicyclic rings of up to 12 carbon atoms, such as phenyl, naphthyl and tetrahydronaphthyl. When R$^5$ and R$^6$ together with the nitrogen atom form a ring, this is preferably a 5 to 7-membered saturated heterocyclic ring, which may optionally contain a further heteroatom selected from oxygen, sulphur or nitrogen. Suitable rings thus include pyrrolidino, piperidino, piperazino and morpholino.

In the above compounds R$^1$ preferably represents halogen (e.g. bromine), CF$_3$, C$_{1-6}$alkoxy (e.g. methoxy), (CH$_2$)$_n$CN, —(CH$_2$)$_n$CONR$^5$R$^6$, —(CH$_2$)$_n$SO$_2$NR$^5$R$^6$ or C$_{1-6}$alkanoylamino. Most preferably R$^1$ represents a group —(CH$_2$)$_n$CONR$^5$R$^6$ wherein n represents 0 and R$^5$ and R$^6$ each independently represent hydrogen, methyl, ethyl or propyl. Advantageously, R$^5$ and R$^6$ independently represent hydrogen or methyl.

When R$^1$ represents —CO$_2$R$^4$, then R$^4$ preferably represents C$_{1-6}$alkyl.

R$^2$ and R$^3$ each preferably represent hydrogen, methyl or ethyl. Most preferably NR$^2$R$^3$ is —NH$_2$.

For use according to the present invention the compound of formula (I) is preferably a partial agonist.

Suitable physiologically acceptable salts will be apparent to those skilled in the art and include for example acid addition salts such as those formed with inorganic acids e.g. hydrochloric, sulphuric or phosphoric acids and organic acids e.g. succinic, maleic, acetic or fumaric acid. Other non-physiologically acceptable salts e.g. oxalates may be used for example in the isolation of compounds of formula (I), and are included within the scope of this invention. Also included within the scope of the invention are solvates and hydrates of compounds of formula (I).

It is believed that compounds of formula (I) wherein $R^2$ and $R^3$ both represent hydrogen are novel. Thus in a further aspect the present invention provides compounds of formula (IA):

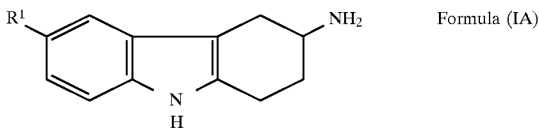

Formula (IA)

wherein $R^1$ is as hereinbefore defined, and salts thereof.

The present invention further provides the following specific compounds which are also believed to be novel:
3-Amino-6-cyano-1,2,3,4-tetrahydrocarbazole hydrochloride,
(+)-3-amino-6-carboxamido-1,2,3,4-tetrahydrocarbazole hydrochloride,
(−)-3-amino-6-carboxamido-1,2,3,4-tetrahydrocarbazole hydrochloride,
3-amino-6-methoxy-1,2,3,4-tetrahydrocarbazole hydrochloride,
3-amino-6-bromo-1,2,3,4-tetrahydrocarbazole hydrochloride,
3-amino-6-methyl-1,2,3,4-tetrahydrocarbazole oxalate,
3-amino-6-ethoxycarbonyl-1,2,3,4-tetrahydrocarbazole oxalate,
3-amino-6-(N-methyl carboxamido)-1,2,3,4-tetrahydrocarbazole hemioxalate,
3-amino-6-cyanomethyl-1,2,3,4-tetrahydrocarbazole oxalate,
3-amino-6-(N-methylsulphonamidomethyl)-1,2,3,4-tetrahydrocarbazole oxalate,
3-amino-6-chloro-1,2,3,4-tetrahydrocarbazole oxalate,
3-amino-6-trifluoromethyl-1,2,3,4-tetrahydrocarbazole oxalate,
3-amino-6-n-butyloxy-1,2,3,4-tetrahydrocarbazole oxalate,
3-amino-6-sulphonamido-1,2,3,4-tetrahydrocarbazole oxalate,
3-amino-6-nitro-1,2,3,4-tetrahydrocarbazole oxalate,
3-amino-6-(N,N-dimethylcarboxamido)-1,2,3,4-tetrahydrocarbazole hemioxalate,
3-amino-6-(piperidin-1-ylcarbonyl)-1,2,3,4-tetrahydrocarbazole hydrochloride,
3-amino-6-(pyrrolidin-1-ylcarbonyl)-1,2,3,4-tetrahydrocarbazole hydrochloride,
3-amino-6-(N,N-diethylcarboxamido)-1,2,3,4-tetrahydrocarbazole hydrochloride,
3-Amino-6-(acetamido)-1,2,3,4-tetrahydrocarbazole oxalate,
3-amino-6-methanesulphonamido-1,2,3,4-tetrahydrocarbazole oxalate,
3-amino-6-carboxamidomethyl-1,2,3,4-tetrahydrocarbazole hydrochloride,
3-methylamino-6-carboxamido-1,2,3,4-tetrahydrocarbazole oxalate,
3-ethylamino-6-carboxamido-1,2,3,4-tetrahydrocarbazole oxalate,
3-n-propylamino-6-carboxamido-1,2,3,4-tetrahydrocarbazole oxalate,
3-i-propylamino-6-carboxamido-1,2,3,4-tetrahydrocarbazole oxalate,
3-dimethylamino-6-carboxamido-1,2,3,4-tetrahydrocarbazole oxalate,
3-benzylamino-6-carboxamido-1,2,3,4-tetrahydrocarbazole oxalate,
3-pyrrolidinyl-6-carboxamido-1,2,3,4-tetrahydrocarbazole oxalate, and
3-(N-(methyl)ethylamino)-6-carboxamido-1,2,3,4-tetrahydrocarbazole oxalate,
3-amino-6-(2-carboxamidoethyl)-1,2,3,4-tetrahydrocarbazole oxalate.

In a further aspect the present invention provides a novel compound of formula (I) e.g. a compound of formula (IA) or any of the above-named compounds (in free base form or as a physiologically acceptable salt) for use as a therapeutic agent, in particular as a 5-$HT_1$-like agonist or partial agonist, for example for the treatment of migraine.

The invention also provides a process for the preparation of novel compounds of formula (I).

Compounds of formula (I) may be prepared by methods known in the art for the preparation of tetrahydrocarbazoles, for example:

A) Reaction of a compound of formula (II):

Formula (II)

(wherein $R^1$ is as hereinbefore defined) or an acid addition salt thereof with a compound of formula (III):

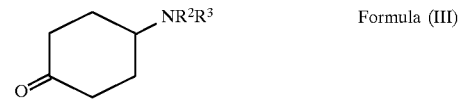

Formula (III)

(wherein $R^2$ and $R^3$ are as hereinbefore defined) or an N-protected derivative thereof; or B) Reaction of a compound of formula (IV):

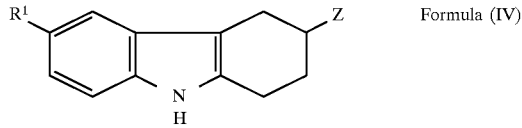

Formula (IV)

(wherein $R^1$ is as defined for formula (I) and Z is a leaving group) with a compound of formula $HNR^2R^3$;

C) Reacting a compound of formula (V):

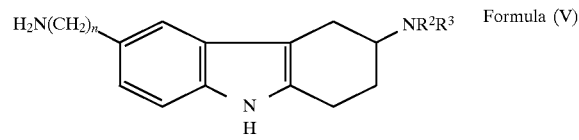

Formula (V)

with an acylating or sulphonylating agent;

D) Conversion of one compound of formula (I) into another compound of formula (I) eg.

(i) to prepare a compound of formula (I) wherein $R^1$ represents —$(CH_2)_nCONH_2$ or $CO_2R^4$, hydrolysis of a compound of formula (I) wherein $R^1$ represents —$(CH_2)_nCN$, or an N-protected derivative thereof;

(ii) to prepare a compound of formula (I) wherein $R^1$ represents —$CONR^5R^6$, amination of a compound of formula (I) wherein $R^1$ represents —$CO_2H$, or an N-protected derivative thereof; or (iii) to prepare a compound of formula (I) wherein one of $R^2$ and $R^3$ is hydrogen and the other is $C_{1-6}$alkyl, alkylation of a compound (I) in which $R^2$ and $R^3$ are both hydrogen;

(iv) to prepare a compound of formula (I) wherein $R^1$ represents hydroxy, cleavage of a compound wherein $R^1$ represents alkoxy or aralkoxy;

followed if necessary by deprotection of any protected nitrogen atoms and if desired by salt formation.

Process (A), which is a form of the Fischer indole synthesis, may be carried out using methods well known in the art. Thus, the reaction may be effected in a solvent, for example an alcohol such as ethanol or butanol; or acetic acid, and at a temperature in the range 0° to 150° C.

Hydrazines of formula (II), which are usually employed as the hydrochloride salt, are known compounds, or may be prepared by conventional methods.

A cyclohexanone of formula (III) may be prepared by oxidation of the corresponding cyclic alcohol, using an oxidising agent such as pyridinium chlorochromate, pyridinium dichromate, dipyridine Cr (VI) oxide, sodium hypochlorite, calcium hypochlorite or manganese dioxide.

The leaving group Z in the compounds of formula (IV) may be for example a halogen atom, or a sulphonyloxy group eg. p-toluenesulphonyloxy or methanesulphonyloxy. Process (B) may be effected in an inert organic solvent, such as an alcohol eg. methanol or an ether eg. tetrahydrofuran and at a temperature in the range 0° to 150° C. Compounds of formula (IV) may be obtained by reacting a hydrazine of formula (II) with an appropriately substituted cyclohexanone compound. When Z is acyloxy or sulphonyloxy this may be prepared from a compound (IV) wherein Z is hydroxy, using standard procedures. Suitable acylating and sulphonylating agents which may be used in process (C) include carboxylic and suilphonic acid chlorides (e.g. acetyl chloride or methanesulphonylchloride) alkyl esters, activated esters and symmetrical and mixed anhydrides. The reaction may be carried out in an organic solvent such as a haloalkane (e.g. dichloromethane), an amide (e.g. N,N-dimethylformamide; an ether (e.g. tetrahydrofuran) or a tertiary amine such as pyridine. In general a base will also be used, e.g. triethylamine, dimethylaminopyridine, or an alkali metal carbonate or bicarbonate. The reaction may be effected at a temperature in the range of −10° to 100° C.

Compounds of formula (V) may be prepared by methods analogous to processes (A) and (B) hereinbefore described. Alternatively a compound of formula (V) may be obtained by subjecting a compound of formula (I) wherein $R^1$ is nitro to reduction, e.g. by catalytic hydrogenation.

It is well known in the chemical art that hydrolysis of a nitrile initially results in an amide, which can be further hydrolysed to an acid. It will therefore be appreciated that the precise product of process (Di) will depend upon the reaction conditions chosen for the hydrolysis. To obtain a compound wherein $R^1$ represents $H_2NCO$— the hydrolysis is preferably effected using hydrogen peroxide in the presence of an alkali hydroxide e.g. sodium hydroxide, in a solvent such as an alcohol e.g. methanol. Other suitable means of hydrolysis include acetic acid and $BF_3$; or formic acid and hydrobromic or hydrochloric acid. To prepare a compound wherein $R^1$ represents —COOH acid or base catalysed hydrolysis may be used.

Process (Dii) may be effected by reacting a compound of formula (I) wherein $R^1$ is —$CO_2H$ with an amine $HNR^5R^6$, in the presence of a coupling agent e.g. dicyclohexylcarbodiimide or N,N'-carbonyldiimidazole. Alternatively the carboxylic acid starting material may first be reacted to form an activated derivative of the carboxyl group, for example an acid chloride, acid anhydride or activated ester, which is then reacted directly with an amine $HNR^5R^6$. The carboxylic acid may also be activated in situ for example by treating with hexamethylphosphoroustriamide.

Alkylation according to process (Diii) may be effected by reacting an amine of formula (I) with an acylating agent, for example an anhydride, such as acetic or propionic anhydride, to form an intermediate in which one of $R^2$ or $R^3$ is —$C(O)C_{1-6}$alkyl, followed by reduction of said intermediate to give the desired product. Other reagents and conditions will be apparent to those skilled in the art.

Cleavage according to process (Div) may be effected by reduction, using methods well known in the art.

It will be appreciated that in many of the above reactions it will be necessary to protect the group —$NR^2R^3$ when one or both of the groups $R^2$ and $R^3$ represent hydrogen. Suitable N-protecting groups are well-known in the art and include for example acyl groups such as acetyl, trifluoroacetyl, benzoyl, methoxycarbonyl, t-butoxycarbonyl, benzyloxycarbonyl or phthaloyl; and aralkyl groups such as benzyl, diphenylmethyl or triphenylmethyl. When $R^2$ and $R^3$ both represent hydrogen the nitrogen atom is preferably protected as the phthalimide. The protecting groups should be easily removable at the end of the reaction sequence. N-deprotection may be effected by conventional methods, for example a phthaloyl group may be removed by reaction with hydrazine; an acyl group such as benzoyl may be cleaved by hydrolysis and an aralkyl group such as benzyl may be cleaved by hydrogenolysis.

When a compound of formula (I) is obtained as a mixture of enantiomers these may be separated by conventional methods, for example by reaction of the mixture with a suitable optically active acid such as d-tartaric acid, 1-malic acid, 1-mandelic acid, 1-gulonic acid or 2,3:4,6-di-O-isopropylidene-keto-L-gulonic acid to give two diastereoisomeric salts which may be separated eg. by crystallisation. Alternatively mixtures of enantiomers may be separated by chromatography, for example on a chiral HPLC column.

Compounds of formula (I) have been found to be agonists and partial agonists at $5HT_1$-like receptors and are expected to have utility in the treatment and/or prophylaxis of migraine, and other conditions associated with cephalic pain.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

BIOLOGICAL DATA $5\text{-}HT_1$-like Receptor Screen

Dog Saphenous Vein

Helicoids of dog saphenous vein were set up at 37° C. in modified Krebs solution at a resting force of 10 mN. The solution also contained 1 $\mu$mol/l each of ketanserin prazosin, atropine and mepyramine, 6 $\mu$mol/l cocaine and 200 $\mu$mol/l ascorbate. Nearly isomeric contractions were measured with force transducers on a polygraph. The tissues were exposed twice to 5-hydroxytryptamine (5-HT) 2 $\mu$mol/l followed by washes. A cumulative concentration-effect curve was determined, followed by a curve to 5-HT in the presence of the highest used concentration of test compound. Contractions caused by the test compound were compared with those caused by 5-HT. The intrinsic activity of the test compound was calculated as the ratio of the maximum test compound-induced effect over the effect caused by 2 $\mu$mol/l 5-HT. The $EC_{50}$ of the test compound was estimated from the corresponding effect curve. When appropriate equilibrium dissociation constants Kp were estimated by the method of Marano & Kaumann (1976, J. Pharmacol. Exp. Ther. 198, 518–525).

In this screen the compounds of Examples 2, 4, 5, 6, 9, 10, 11, 13, 17, 18, 21 and 24 had $EC_{50}$'s in the range 0.1 to 15 $\mu$mol.

RABBIT BASILAR ARTERY

METHODS

Experiments were performed in intracranial arteries from rabbit isolated basilar artery in a similar method to one described previously (Parsons and Whalley, 1989. Eur J Pharmacol 174, 189–196.).

In brief, rabbits were killed by overdose with anaesthetic (sodium pentobarbitone). The whole brain was quickly removed and immersed in ice cold modified Kreb's solution and the basilar artery removed with the aid of a dissecting microscope. The Krebs solution was of the following composition (mM) $Na^+$ (120); $K^+$ (5); $Ca^{2+}$ (2.25); $Mg^{2+}$ (0.5); $Cl^-$ (98.5); $SO_4^{2-}$ (1); EDTA (0.04), equilibrated with 95% $O_2$/5% $CO_2$. The endothelium was removed by a gentle rubbing of the lumen with a fine metal wire. Arteries were then cut into ring segments (ca 4–5 mm wide) and set up for recording of isometric tension in 50 ml tissue baths in modified Krebs solution with the additional supplement of (mM); $Na^{2+}$ (20); fumarate (10); pyruvate (5); L-glutamate (5) and glucose (10). The arteries were then placed under a resting force of 3–4 mN maintained at 37° C. and the solution bubbled with 95% $O_2$/5% $CO_2$.

After tests for initial reactivity with 90 mM KCl depolarising solution and for lack of acetylcholine-induced relaxation of 5-HT (10 mM) precontraction, cumulative concentration-effect curves (2 nM-60 mM) to 5-HT were constructed in the presence of ascorbate 200 mM, cocaine 6 mM, indomethacin 2.8 mM, ketanserin 1 mM and prazosin 1 mM.

Following a 45–60 min wash period, cumulative concentration-effect curves to the test compounds or 5-HT (as a time match control) were constructed in the presence of ascorbate, indomethacin, cocaine, ketanserin and prazosin.

In this screen the compounds of Example 2, 5, 6, 15, 17, 24, 25, 26, 28 and 29 had $EC_{50}$'s in the range 0.04 to 15.

Example 1

3-Amino-6-cyano-1,2,3,4-tetrahydrocarbazole hydrochloride

A solution of 4-aminocyclohexanol hydrochloride (6.08 g, 0.04 mole) in water (60 ml) was brought to pH 8 with aqueous sodium bicarbonate solution. N-carbethoxyphthalimide (8.76 g, 0.04 mole) was added followed by tetrahydrofuran (until homogenous solution was obtained). The clear solution was stirred at room temperature overnight. During this time a white solid was precipitated. The tetrahydrofuran was removed in vacuo and the remaining aqueous solution was extracted with ethyl acetate until the solution was clear. The ethyl acetate extracts were combined, washed with water, dried (MgSO$_4$) and concentrated to give 4-phthalimido cyclohexanol as a white solid (7.1 g).

A solution of 4-phthalimido cyclohexanol (7.1 g, 0.029 mole) in dichloromethane (250 ml) was treated with pyridinium chlorochromate (8.6 g, 0.04 mole) and the resulting dark mixture was stirred at room temperature overnight. Diethyl ether (50 ml) was added and the mixture filtered through keiselguhr. The filtrate was concentrated in vacuo and the residue purified by column chromatography (SiO$_2$; CHCl$_3$/EtOAc) to give 4-phthalimido cyclohexanone as a white solid (6.4 g).

4-Cyanophenyl hydrazine hydrochloride (4.41 g, 0.026 mole) was dissolved in acetic acid (100 ml) and sodium acetate (2 g) was added. 4-Phthalimido cyclohexanone (6.4 g, 0.026 mole) was added and the mixture heated under reflux overnight. The solvent was removed in vacuo and the residue triturated with methanol to give 3-phthalimido-6-cyano-1,2,3,4-tetrahydrocarbazole as a beige solid, (5.3 g).

A suspension of the above product (1 g) in ethanol (40 ml) was treated with hydrazine in water (10 ml). The reaction mixture was stirred at room temperature overnight during which time the reactants dissolved. The solvent was removed in vacuo and the residue partitioned between aqueous potassium carbonate and ethyl acetate. The ethyl acetate solution was washed with water, dried and concentrated in vacuo to give 3-amino-6-cyano-1,2,3,4-tetrahydrocarbazole as a beige solid (500 mg). This product was converted into the hydrochloride salt to give the title compound, mp 289° C. (dec.).

$^1$H NMR [250 MHz, CD$_3$OD] δ 1.98–2.18 (1H, m), 2.25–2.40 (1H, m), 2.77 (1H, dd), 2.98 (2H, m), 3.22 (1H, dd), 3.68 (1H, m), 7.34 (1H, d), 7.43 (1H, d), 7.82 (1H, s).

Example 2

3-Amino-6-carboxamido-1,2,3,4-tetrahydrocarbazole hydrochloride

The product of Example 1 (400 mg) was dissolved in tetrahydrofuran, and di-t-butyl dicarbonate (500 mg) was added. The mixture was stirred at room temperature overnight. The solvent was removed in vacuo and the residue purified by column chromatography (SiO$_2$; CHCl$_3$/EtOAc) to give 3-t-butyloxycarbonylamino-6-cyano-1,2,3,4-tetrahydrocarbazole (40 mg).

A mixture of the above product nitrile (440 mg), aqueous hydrogen peroxide (30%, 0.5 ml) and sodium hydroxide (aq) (20%, 0.5 ml) in methanol (25 ml) was stirred at room temperature overnight. Sodium metabisulphite (100 mg) was added and the solvent removed in vacuo. The residue was dissolved in ethyl acetate and the ethyl acetate layer was separated, dried and concentrated in vacuo to give a gummy solid which was purified by column chromatography (SiO$_2$; CHCl$_3$/ EtOAc) to give 3-t-butyloxycarbonylamino-6-carboxamido-1,2,3,4-tetrahydrocarbazole as a white solid (400 mg), mp 270° C. (dec).

The above product (400 mg, 0.0012 mole) was dissolved in dioxan (100 ml) and HCl gas was bubbled through the solution for 20 minutes. During this time a white solid was precipitated. Excess hydrogen chloride was swept from the solution by bubbling through N$_2$, and the solid product, 3-amino-6-carboxamido-1,2,3,4-tetrahydrocarbazole hydrochloride was collected by filtration, washed with diethyl ether and dried to give the title compound as a white solid (300 mg). m.p. 270 (dec).

$^1$H NMR [250 MHz, DMSO-d$^6$] δ 1.96 (1H, m), 2.16–2.30 (1H, m), 2.74 (1H, dd), 2.85 (2H, m), 3.12 (1H, dd), 1 signal obscured by H$_2$O at ca. 3.6, 7.08 (1H, brd.s), 7.27 (1H, d), 7.61 (1H, d), 7.87 (1H, brd.s), 7.99 (1H, s), 8.39 (3H, brd.s).

Example 3

3-Amino-6-methoxy-1,2,3,4-tetrahydrocarbazole hydrochloride

Reaction of 4-methoxyphenyl hydrazine hydrochloride (0.87 g, 5.0 mmol) with 4-phthalimido-cyclohexanone (1.22 g, 5.0 mmol) in ethanol (20 ml) heated under reflux for 2 hr, followed by cooling and removal of the precipitated solid by filtration gave 3-phthalimido-6-methoxy-1,2,3,4-tetrahydrocarbazole (1.62 g).

The above product (1.57 g, 4.5 mmol) was suspended in ethanol (100 ml) and treated with hydrazine hydrate (23 ml) while stirring at room temperature. After 30 min, the solvent was removed in vacuo and the residue was partitioned between K$_2$CO$_3$ (aq) and EtOAc. The latter layer was separated, washed with water, dried (MgSO$_4$) and evaporated to dryness. This residue was dissolved in ethanol and treated with ethereal HCl until cloudy, then left to stand overnight to yield the title compound (0.95 g) mp>250° C. $^1$H NMR [250 MHz, DMSO-d$^6$] δ 1.81–2.02 (1H, m), 2.10–2.28 (1H, m), 2.65 (1H, dd), 2.82 (2H, m), 3.02 (1H, dd), 1 signal obscured by H$_2$O at ca. 3.5, 3.74 (3H, s), 6.66 (1H, d), 6.84 (1H, d), 7.14 (1H, d), 8.16 (3H, brd.s)

Example 4

3-Amino-6-bromo-1,2,3,4-tetrahydrocarbazole hydrochloride

Reaction of 4-bromophenylhydrazine hydrochloride (4.0g, 18.1 mmol) with 4-phthalimido-cyclohexanone (4.39g, 18.1 mmol) in refluxing n-butanol for 20 min, followed by cooling, filtration, and evaporation of the filtrate to dryness yielded 3-phthalimido-6-bromo-1,2,3,4-tetrahydrocarbazole as an orange solid (7.45g).

This product (0.33g, 0.83 mmol) was suspended in ethanol (13 ml) and treated with hydrazine hydrate (3 ml), then left to stir at room temperature overnight. The solid precipitate was filtered off, and the filtrate was evaporated to dryness and partitioned between K$_2$CO$_3$ (aq) and ethylacetate. After separation of the organic layer, washing with water, drying (MgSO$_4$) and evaporation to dryness, the residue was dissolved in MeOH and treated with HCl gas. Solvent was removed in vacuo and the residue was crystallized from ethanol/ethyl acetate to yield the title compound as a cream-coloured solid (0.15g), mp 308°–310° C. $^1$H NMR [250 MHz, DMSO-d$^6$]δ 1.91 (1H, m), 2.10–2.26 (1H, m) 2.63 (1H, dd), 2.84 (2H, m), 3.04 (1H, dd), 3.50 (1H, m), 7.12 (1H, d), 7.24 (1H, d), 7.55 (1H, s), 8.15 (2H, brd.s), 11.12 (1H, s).

Example 5

3-Amino-6-carboxamido-1,2,3,4-tetrahydrocarbazole

4-Carboxamidophenylhydrazine hydrochloride (2.87 g) and 4-phthalimidocyclohexanone (3.00 g) were mixed in acetic acid and the mixture was heated under reflux for 2 hr. After cooling, the mixture was neutralized using aq. potassium carbonate solution, and the yellow solid thus obtained was filtered, washed with water, and dried. Purification by column chromatography (SiO$_2$; CHCl$_3$/CH$_3$OH) gave 3-phthalimido-6-carboxamido-1,2,3,4-tetrahydrocarbazole (2.8 g).

The above product (1.0 g) was suspended in ethanol (10 ml) and hydrazine hydrate (5 ml) was added. A clear solution was obtained, and the mixture was left to stir overnight, to yield a precipitate. The whole mixture was evaporated to dryness, washed with aq. $K_2CO_3$ solution, and water, to leave the title compound 3-amino-6-carboxamido-1,2,3,4-tetrahydrocarbazole (0.44 g), as the monohydrate, mp. 146°–148° C. $^1$H NMR [250 MHz, DMSO-d$^6$] δ 1.49–1.77 (1H,m), 1.83–2.03 (1H,m), 2.17–2.40 (1H,m), 2.62–2.80 (2H,m), 2.90 (1H,dd), 1 signal obscured by $H_2O$ at ca. 3.1, 7.03 (1H,brd.s), 7.18 (1H,d), 7.58 (1H,d), 7.83 (1H,brd.s), 7.98 (1H,s).

Example 6

(+)- and (−)- 3-Amino-6-carboxamido-1,2,3,4-tetrahydrocarbazole hydrochloride

Method 1

(±)-3-t-Butyloxycarbonylamino-6-carboxamido-1,2,3,4-tetrahydrocarbazole was separated into its enantiomers using chiral HPLC: (chiralcel OD 4.6 mm column, eluting with hexane/ethanol 85:15). The (+)-enantiomer was collected first and had mp =150°–152° C. and $[\alpha]_D^{25}$=+70.1 (in methanol, 0.41% w/v). The (−)-enantiomer had mp=150°–152° C. and $[\alpha]_D^{25}$=−79.4 (in methanol, 0.40% w/v). The (+)-enantiomer was converted to the parent amine hydrochloride by treating with HCl gas in dioxane, to furnish the (+)-enantiomer of 3-amino-6-carboxamido-1,2,3,4-tetrahydrocarbazole hydrochloride, mp=248°–251° C., $[\alpha]_D^{25}$=+26.2 (in methanol, 0.50% w/v). The (−)-enantiomer of 3-t-butyloxycarbonylamino-6-carboxamido-1,2,3,4-tetrahydrocarbazole was similarly converted into the (−)-enantiomer of 3-amino-6-carboxamido-1,2,3,4-tetrahydrocarbazole hydrochloride, mp=248°–251° C., $[\alpha]_D^{25}$=−28.6 (in methanol, 0.50% w/v).

Method 2

(±)-6-carboxamido-3-amino-1,2,3,4-tetrahydrocarbazole was treated with one equivalent of 2,3:4,6-di-O-isopropylidene-2-keto-L-gulonic acid in methanol to give the salt of the (+)-enantiomer, in 38% yield (with respect to racemate) and 84% enantiomeric excess (ee). This material was recrystallized twice from methanol to give the salt of the (+)-enantiomer in 25% overall yield (with respect to racemate), and >98% ee. This product was converted to the hydrochloride salt first by treatment with aqueous alkali, and the precipitated free base treated with 2M aq. HCl in ethanol, to give (+)- 3-amino-6-carboxamido-1,2,3,4-tetrahydrocarbazole hydrochloride.

Example 7

3-Amino-6-methyl-1,2,3,4-tetrahydrocarbazole oxalate

Reaction of 4-phthalimidocyclohexanone (2.16 g) with 4-tolylhydrazine hydrochloride (1.41 g), and subsequent deprotection of the product by the method described in example 3, gave the title compound free base, which was converted to the oxalate salt (0.23 g), mp 272°–5° C.

Example 8

3-Amino-6-ethoxycarbonyl-1,2,3,4-tetrahydrocarbazole oxalate

Reaction of 4-phthalimidocyclohexanone (0.37 g) with 4-ethoxycarbonylphenylhydrazine hydrochloride (0.33 g), and subsequent deprotection by the method described in example 3, gave the title compound free base. This was converted to the oxalate salt (0.11 g), mp 230°–240° C. dec.

Example 9

3-Amino-6-(N-methyl carboxamido)-1,2,3,4-tetrahydrocarbazole hemioxalate

Reaction of 4-phthalimidocyclohexanone (1.20 g) with 4-(N-methylcarboxamido)-phenylhydrazine hydrochloride (1.00 g), and subsequent deprotection by the method described in example 3, gave the title compound free base. This was converted to the hemioxalate salt (0.22 g), mp 227° C. dec.

Example 10

3-Amino-6-cyanomethyl-1,2,3,4-tetrahydrocarbazole oxalate

Reaction of 4-phthalimidocyclohexanone (1.05 g) with 4-cyanomethylphenylhydrazine hydrochloride (0.79 g), and subsequent deprotection by the method described in example 3, gave the title compound free base, which was treated with oxalic acid to give the oxalate salt (0.49 g), mp 219°–224° C. dec.

Example 11

3-Amino-6-(N-methylsulphonamidomethyl)-1,2,3,4-tetrahydrocarbazole oxalate

Reaction of 4-phthalimidocyclohexanone (0.42 g) with 4-(N-methylsulphonamidomethyl) phenyl hydrazine hydrochloride (0.44 g), and subsequent deprotection by the method described in example 3, gave the title compound free base. This was treated with oxalic acid to give the oxalate salt (0.15 g), mp 218°–222° C. dec.

Example 12

3-Amino-6-chloro-1,2,3,4-tetrahydrocarbazole oxalate

Reaction of 4-phthalimidocyclohexanone (6.7 g) with 4-chlorophenyl hydrazine hydrochloride (4.93 g), and subsequent deprotection by the method described in example 3, gave the title compound free base, which was treated with oxalic acid to give the oxalate salt (2.77 g), dec >220° C.

Example 13

3-Amino-6-trifluoromethyl-1,2,3,4-tetrahydrocarbazole oxalate

Reaction of 4-phthalimidocyclohexanone (1.14 g) with 4-trifluoromethyl phenyl hydrazine hydrochloride (1.00 g), and subsequent deprotection by the method described in example 3, gave the title compound free base (0.40 g). This was treated with oxalic acid to give the oxalate salt, mp 212°–213° C.

Example 14

3-Amino-6-n-butyloxy-1,2,3,4-tetrahydrocarbazole oxalate

Reaction of 4-phthalimidocyclohexanone (1.12 g) with 4-n-butyloxyphenyl hydrazine hydrochloride (1.00 g) and subsequent deprotection by the method described in example 3, gave the title compound free base. This was treated with oxalic acid to give the oxalate salt (0.47 g), mp 227°–229° C.

Example 15

3-Amino-6-sulphonamido-1,2,3,4-tetrahydrocarbazole oxalate

Reaction of 4-phthalimidocyclohexanone (1.00 g) with 4-sulphonamido phenyl hydrazine hydrochloride (1.08 g), and subsequent deprotection by the method described in example 3, gave the title compound free base. This was converted to the oxalate salt (0.090 g), dec >200° C.

Example 16

3-Amino-6-Nitro-1,2,3,4-tetrahydrocarbazole oxalate

Reaction of 4-phthalimidocyclohexanone (1.28 g) with 4-nitrophenyl hydrazine hydrochloride (1.00 g), and subsequent deprotection by the method described in example 3, gave the title compound free base, which was converted to the oxalate salt (0.25 g), mp 275°–277° C.

Example 17

3-Amino-6-(N,N-dimethyl carboxamido)-1,2,3,4-tetrahydrocarbazole hemioxalate

3-Amino-6-ethoxycarbonyl-1,2,3,4-tetrahydrocarbazole (260 mg, 1.0 mmol) was suspended in dry THF (5 ml), and di-tert butyl dicarbonate (320 mg, 1.5 mmol) was added. A clear solution was obtained after 10 min. The mixture was left to stir for 20 hr. then the solvent was removed, and the residue was dissolved in ethyl acetate, washed with aqueous sodium bicarbonate solution, and dried ($MgSO_4$). After removal of ethyl acetate, the residue was triturated with ether and hexane to give 3-t-butyloxycarbonylamino-6-ethoxycarbonyl-1,2,3,4-tetrahydrocarbazole (310 mg).

The above product (556 mg, 1.55 mmol) was suspended in ethanol (5 ml) and 2M NaOH (3 ml) was added. The mixture was heated under reflux for 1 hr and evaporated to dryness. The residue was dissolved in water and neutralized with acetic acid, when 3-t-butyloxycarbonylamino-6-carboxy-1,2,3,4-tetrahydrocarbazole precipitated out as a white solid (425 mg). A solution of the above product (400 mg, 1.2 mmol) in dry DMF (8 ml) was treated with hexamethyl phosphorous triamide (198 mg, 1.2 mmol), and cooled to −10° C. Dimethylamine gas was bubbled into the mixture for 10 min at this temperature, then carbon tetrachloride (185 mg, 1.2 mmol) was added dropwise, under an atmosphere of nitrogen. The mixture was left to stir at room temperature for 1 hr, then the DMF was removed in vacuo. The residue was partitioned between ethyl acetate and water, and the organic layer was washed with saturated aqueous sodium bicarbonate solution, then brine, and dried ($MgSO_4$). The solvent was removed in vacuo, and the residual oil was triturated with ether and hexane and the solid recrystallized from toluene to give 3-t-butyloxycarbonylamino-6-(N,N-dimethyl carboxamido)-1,2,3,4-tetrahydrocarbazole (198 mg).

This product (180 mg, 0.53 mmol) was dissolved in dioxane (5 ml) and HCl gas was bubbled through, to precipitate an oil. The solvent was removed in vacuo, and the oil was dissolved in water, and treated with $K_2CO_3$ solution to bring the pH to 12. The amine free base was then extracted with ethyl acetate, dried ($MgSO_4$) and evaporated to dryness. The resulting oil was dissolved in methanol and treated with oxalic acid to provide the title compound as a pale pink solid (140 mg) mp=190°–195° C.

Example 18

3-Amino-6-(piperidin-1-yl carbonyl)-1,2,3,4-tetrahydrocarbazole hydrochloride

Reaction of 3-t-butyloxycarbonylamino-6-carboxy-1,2,3,4-tetrahydrocarbazole (175 mg) with piperidine and the product subsequently deprotected by the method described for Example 17, gave the title compound, mp =246°–249° C. (55 mg).

Example 19

3-Amino-6-(pyrrolidin-1-yl carbonyl)-1,2,3,4-tetrahydrocarbazole hydrochloride

Reaction of 3-t-butyloxycarbonylamino-6-carboxy-1,2,3,4-tetrahydrocarbazole (140 mg) with pyrrolidine, and the product subsequently deprotected as described for Example 17, gave the title compound, mp=201°–212° C. (81 mg).

Example 20

3-Amino-6-(N,N-diethyl carboxamido)-1,2,3,4-tetrahydrocarbazole hydrochloride

Reaction of 3-t-butyloxycarbonylamino-6-carboxy-1,2,3,4-tetrahydrocarbazole (105 mg) with diethylamine, and deprotection of the product, as described for Example 17, gave the title compound, mp 200°–205° C. (50 mg).

Example 21

3-Amino-6-(acetamido)-1,2,3,4-tetrahydrocarbazole oxalate

Reaction of 4-phthalimido cyclohexanone (1.2 g) with 4-(acetamido)-phenyl hydrazine hydrochloride (1.0 g), and subsequent deprotection of the product by the method described in example 3, gave the title compound free base (570 mg). A portion of this product (50 mg) was treated with oxalic acid in methanol to give the oxalate salt, which softens >170° C. (38 mg).

Example 22

3-Amino-6-methanesulphonamido-1,2,3,4-tetrahydrocarbazole oxalate 3-phthalimido-6-nitro-1,2,3,4-tetrahydrocarbazole (4.00 g) was dissolved in hot ethyl acetate (130 ml). To the cooled solution was added raney nickel, and the mixture was hydrogenated at an initial pressure of 39 psi at room temperature for 4 hr. After filtering off the insoluble materials, the filtrate was evaporated to dryness, and extracted twice into 20% aqueous methanol and the extracts combined and reduced in volume to give 3-phthalimido-6-amino-1,2,3,4-tetrahydrocarbazole (0.31 g).

The above product (0.50 g) was dissolved in freshly distilled pyridine (30 ml), and methanesulphonyl chloride (0.28 g) and 4-dimethylaminopyridine (46 mg) were added. The mixture was heated with stirring at 50° C. for 5 hr, and then evaporated to dryness. The residue was dissolved in chloroform, washed with water, brine and aqueous sodium bicarbonate, then dried ($MgSO_4$), and evaporated to dryness to give a pale yellow solid, which was recrystallized from aqueous ethanol to give 3-phthalimido-6-methanesulphonamido-1,2,3,4-tetrahydrocarbazole (0.27 g).

The above compound was suspended in ethanol (15 ml) and hydrazine hydrate (2.72 g) was added. After stirring for 25 min at room temperature, the mixture was evaporated to dryness, partitioned between water and ethyl acetate, and the aqueous layer re-extracted with ethyl acetate. The organic extracts were combined, washed with water, dried ($MgSO_4$) and evaporated to give a pale yellow solid. This was dissolved in methanol and treated with oxalic acid (89 mg). Addition of ether resulted in crystallization of the title compound (50 mg), mp 230°–233° C.

Example 23

3-Amino-6-carboxamidomethyl-1,2,3,4-tetrahydrocarbazole hydrochloride

3-Amino-6-cyanomethyl-1,2,3,4-tetrahydrocarbazole (2.5 g) and di-t-butyl dicarbonate (3.63 g) were stirred in THF (56 ml) for 2 hr. The THF was evaporated, and the residue was partitioned between aqueous sodium bicarbonate solution and ethyl acetate. The aqueous phase was re-extracted with ethyl acetate, and the combined organic extracts were washed with water, dried ($MgSO_4$), and evaporated to dryness to leave a solid which was triturated with ether/hexane (20%) to give 3-t-butyloxycarbonylamino-6-cyanomethyl-1,2,3,4-tetrahydrocarbazole as an off-white solid (3.44 g).

The above product (7.0 g) was dissolved in DMSO (70 ml), and hydrogen peroxide (100 volume, 3.5 ml) was added. After stirring for an hour, further peroxide (8.5 ml) was added, and the mixture was stirred for 2 hr at room temperature. Potassium carbonate (0.84 g) was added, and the mixture was stirred overnight and for a further 20 hr. The reaction mixture was poured into water (500 ml) and the resulting white solid was filtered off, and recrystallized from methanol to give 3-t-butyloxycarbonylamino-6-carboxamidomethyl-1,2,3,4-tetrahydrocarbazole (5.42 g).

The above product (500 mg) was dissolved in dry dioxane (30 ml), and HCl gas was bubbled through for 20 min. The resulting solution and deposited gum were evaporated to dryness, and treated with aqueous potassium carbonate solution. This was extracted with ethyl acetate, and the extracts were combined, dried ($MgSO_4$) and evaporated to dryness. The residue was dissolved in methanol and treated with excess oxalic acid. Addition of ether led to crystallization of the title compound (250 mg), mp 257°–260° C.

Example 24

3-Methylamino-6-carboxamido-1,2,3,4-tetrahydrocarbazole hydrochloride

4-Cyanophenyl hydrazine hydrochloride (20.2 g) and 4-benzoyloxycyclohexanone (25.9 g) were dissolved in glacial acetic acid (400 ml) and the mixture was heated under reflux for 1.5 hr. After allowing to cool, the mixture was filtered, and the filtrate was evaporated to dryness, and neutralized with aqueous sodium bicarbonate solution to give a solid precipitate, which was purified by chromatography ($SiO_2$; hexane/ethyl acetate) to give 3-benzoyloxy-6-cyano-1,2,3,4-tetrahydrocarbazole (18 g). This product (11.6 g) was suspended in ethanol (230 ml) and treated with 2.5% aqueous potassium hydroxide solution (120 ml), and heated under reflux for 1 hr. The cooled mixture was neutralized with glacial acetic acid and evaporated to a solid residue, which was washed with water, and dried to give 3-hydroxy-6-cyano-1,2,3,4-tetrahydrocarbazole (6.6 g).

The above product (3.57 g) was dissolved in dry pyridine (35 ml) and treated with tosyl chloride (3.51 g) in dry pyridine (35 ml), and the mixture was stirred at 100° C. for 2 hr. After cooling, the solution was poured into water (500 ml), extracted with ethyl acetate, and the latter extract was washed with 2M HCl, dried ($MgSO_4$) and evaporated to dryness. Purification by chromatography (SiO2; hexane/ethyl acetate) gave 3-tosyloxy-6-cyano-1,2,3,4-tetrahydrocarbazole (0.53 g).

This product (0.40 g) was dissolved in 33% methylamine in alcohol (25 ml) and heated at 100° C. in a sealed steel vessel for 1.5 hr. After cooling, the mixture was evaporated to dryness and purified by chromatography ($SiO_2$; chloroform/methanol) to give 3-methylamino-6-cyano-1,2, 3,4-tetrahydrocarbazole (0.13 g).

The above product (0.12 g) was dissolved in THF (10 ml) and reacted with di-tert-butyl dicarbonate (0.36 g) in THF (3 ml) at room temperature overnight. The reaction mixture was evaporated to dryness, partitioned between 2M sodium bicarbonate solution and ethyl acetate, and the organic extract dried and evaporated to give a white solid. This was triturated with ether/hexane to give 3-t-butyloxycarbonylmethyl amino-6-cyano-1,2,3,4-tetrahydrocarbazole (0.14 g).

This product (0.14 g) was dissolved in methanol (15 ml) and treated with a mixture of 20% aqueous sodium hydroxide (0.20 ml) and 30% hydrogen peroxide (0.20 ml), and the whole mixture was stirred at room temperature overnight. Sodium metabisulphite (38 mg) was added, and the solution was evaporated to dryness, and chromatographed ($SiO_2$; chloroform/10% $NH_4OH$ in methanol) to give 3-methylamino-6-carboxamido-1,2,3,4-tetrahydrocarbazole (0.12 g). The above compound (0.11 g) was dissolved in methanol (10 ml), and treated with 3M hydrochloric acid at room temperature. The mixture was evaporated to dryness, azeotroping with ethanol to give a solid, which was recrystallized from methanol/ether to give the title compound, mp 327°–328° C. (80 mg).

$^1$H NMR [250 MHz, MeOH-$d^4$] d 1.98–2.20 (1H, m), 2.29–2.49 (1H, m), 2.75–2.90 (5H, s+m), 2.90–3.09 (2H, m), 3.52–3.69 (1H, m), 7.31 (1H, d), 7.63 (1H, d), 8.05 (1H, s).

Example 25

3-Ethylamino-6-carboxamido-1,2,3,4-tetrahydrocarbazole oxalate 1,4-Cyclohexanedione mono-2',2'-dimethyl trimethylene ketal (2.00 g) was mixed with anhydrous ethylamine (10.0 g) and benzene (10 ml), and the mixture was cooled to 5° C. A solution of titanium tetrachloride (0.95 g) in benzene (10 ml) was added, dropwise, then the mixture was stirred at room temperature for 1 hr. The mixture was filtered, and evaporated to dryness to give an oil, which was dissolved in ethanol (30 ml). To this solution was added palladium-on-carbon catalyst (100 mg), and the mixture was hydrogenated at 50 psi pressure overnight. The catalyst was filtered off and the ethanol evaporated to leave 4-ethylamino-cyclohexanone 2',2'-dimethyl trimethylene ketal as an oil (2.0 g).

This compound (0.80 g) was dissolved in formic acid (20 ml) and the solution was heated to 90° C. for 1 hr. Formic acid was evaporated, and the residue was partitioned between chloroform and 1M hydrochloric acid. The aqueous layer was evaporated to dryness to give 4-ethylaminocyclohexanone (0.40 g).

A mixture of the above product (0.40 g) and 4-carboxamidophenyl hydrazine hydrochloride (0.60 g) in glacial acetic acid (20 ml) was heated under reflux for 1 hr. The acid was evaporated in vacuo to an oil, which was purified by chromatography ($SiO_2$; $CHCl_3$/10% $NH_3$ in MeOH) to give an oil (0.50 g). Part of this product (150 mg) was dissolved in methanol and treated with oxalic acid. The solution was treated with ether to give the title compound as a crystalline solid, mp 165°–170° C. (100 mg).

1H NMR [250 MHz, DMSO-$d^6$] d 1.25 (3H, t), 1.81–2.05 (1H, m), 2.20–2.38 (1H, m), 2.61–2.79 (1H, m), 2.79–2.94 (2H, m), 2.98–3.28 (3H, dd+s), 3.41–3.60 (1H, m), 7.08 (1H, brd. s), 7.28 (1H, d), 7.60 (1H, d), 7.82 (1H, brd. s), 8.00 (1H, s), 11.12 (1H, s).

Example 26

3-n-Propylamino-6-carboxamido-1,2,3,4-tetrahydrocarbazole oxalate

Propylamine (1.81 g) was dissolved in methanol (12.5 ml), and 1.5M HCl in methanol (6.6 ml) was added with cooling. After 1 min, 1,4-cyclohexanedione mono-2',2'-dimethyl trimethylene ketal (1.0 g) was added, followed after a further 10 min by sodium cyanoborohydride (0.23 g). The mixture was stirred at room temperature for 3 days. The resulting mixture was filtered, and the filtrate was evaporated and treated with 1M HCl (10 ml) with cooling. The residue was digested to form a solution, which was washed with ether, basified to pH 12 with aqueous sodium hydroxide, and extracted with dichloromethane. This extract was washed with saturated aqueous sodium bicarbonate solution, dried ($MgSO_4$), and evaporated to dryness. Chromatography ($SiO_2$; chloroform/methanol/ammonia) gave 4-n-propylamino cyclohexanone 2',2'-dimethyl trimethylene ketal (0.72 g).

This product (0.66 g) was hydrolyzed to the ketone, which was reacted with 4-carboxamidophenyl hydrazine hydrochloride and converted to the oxalate salt as described for Example 25, to give the title compound (0.44 g), mp >168° C. dec.

Example 27

3-i-Propylamino-6-carboxamido-1,2,3,4-tetrahydrocarbazole oxalate

Reaction of isopropylamine (9.54 g) with 1,4-cyclohexanedione mono-2',2'-dimethyl trimethylene ketal (2.0 g) by the method described for Example 25 gave 4-i-propylamino cyclohexanone 2',2'-dimethyl trimethylene ketal (2.38 g). This product (0.66 g) was hydrolyzed and reacted with 4-carboxamidophenyl hydrazine hydrochloride (0.45 g), and the mixture worked up as described above to give the title compound free base (0.34 g). This was converted to the oxalate, mp >235° C. dec.

Example 28

3-Dimethylamino-6-carboxamido-1,2,3,4-tetrahydrocarbazole oxalate

Dimethylamine (10.0 g) was reacted with 1,4-cyclohexanedione mono-2',2'-dimethyl trimethylene ketal (2.0 g) by the method described for Example 25 to give 4-dimethylaminocyclohexanone-2',2'-dimethyl trimethylene ketal (0.72 g). This product (0.72 g) was hydrolyzed and reacted with 4-carboxamidophenyl hydrazine hydrochloride (0.47 g) and the product converted to the oxalate salt as described above to give the title compound (0.20 g), mp 99°–101° C.

$^1$H NMR [250 MHz, DMSO-d$^6$] d 1.83–2.05 (1H, m), 2.27–2.40 (1H, m) 2.72–3.00 (9H, 2m+s), 3.07–3.22 (1H, dd), 3.50–3.68 (1H, m), 7.05 (1H, brd. s), 7.27 (1H, d), 7.60 (1H, d), 7.81 (1H, brd. s), 8.00 (1H, s), 11.11 (1H, s).

Example 29

3-Benzylamino-6-carboxamido-1,2,3,4-tetrahydrocarbazole oxalate

Reaction of benzylamine (0.59 g) with 1,4-cyclohexanedionemono-2',2'-dimethyl trimethylene ketal (1.0 g) and subsequent reduction of the imine with sodium cyanoborohydride by the method described for Example 26 gave 4-benzylaminocyclohexanone 2',2'-dimethyl trimethylene ketal (0.54 g). This product (0.52 g) was reacted with 4-carboxamidophenyl hydrazine hydrochloride (0.34 g) and the product treated with oxalic acid to give the title compound, mp >190° C. dec (0.11 g).

Example 30

3-Pyrrolidinyl-6-carboxamido-1,2,3,4-tetrahydrocarbazole oxalate

Reaction of pyrrolidine (15.6 g) with 1,4-cyclohexanedione mono-2',2'-dimethyl trimethylene ketal (2.0 g) by the method described for Example 25 gave 4-pyrrolidinyl-cyclohexanone-2',2'-dimethyl trimethylene ketal (1.74 g). This product (1.70 g) was hydrolyzed and reacted with 4-carboxamidophenyl hydrazine hydrochloride (1.70 g) and the product treated with oxalic acid as described above to give the title compound (32 mg), mp >190° C. dec.

Example 31

3-(N-methyl ethylamino)-6-carboxamido-1,2,3,4-tetrahydrocarbazole oxalate

Reaction of N-methyl ethylamine (13.0 g) with 1,4-cyclohexanedione mono-2',2'-dimethyl trimethylene ketal (2.0 g) by the method described for Example 25 gave 4-(N-methyl ethylamino)-cyclohexanone-2',2'-dimethyl trimethylene ketal (1.71 g). This product (0.86 g) was hydrolyzed and reacted with 4-carboxamidophenyl hydrazine hydrochloride (0.52 g) and worked up as described above to give the title compound (76 mg), mp >130° C. dec.

Example 32

3-Amino-6-(2-carboxamidoethyl)-1,2,3,4-Tetrahydrocarbazole oxalate

A mixture of 4-nitrocinnamic acid (22.5 g) and thionyl chloride (20.8 g) in benzene (160 ml) was heated under reflux for 4 h. The resulting orange mixture was filtered and evaporated to give the acid chloride (22.9 g). This was dissolved in dichloromethane (1 l), and ammonia gas was bubbled through, with cooling to below 20° C. and stirring. Solvent was removed in vacuo, and the residue was dissolved in hot ethyl acetate and the solution was shaken with 1M sodium hydroxide solution. The resulting organic phase was dried, filtered and evaporated to leave a residue which was slurried with ethyl acetate to give 4-nitro cinnamamide as a crystalline solid (18.6 g). This product (18.6 g) was suspended in ethanol (1 l) and hydrogenated using Pd-C catalyst (6.6 g) at 50 psi for 1 h. The resulting mixture was filtered and evaporated to dryness, providing 4-aminophenyl propionamide (17.1 g).

Concentrated hydrochloric acid (4 ml) was added slowly, with cooling and stirring to 4-aminophenyl propionamide (0.80 g), maintaining the temperature below 5° C. To this slurry was added a solution of sodium nitrite (0.37 g) in water (2 ml), dropwise over 15 min, followed by stirring for a further 15 min. The turbid solution thus formed was added portionwise to a cooled, stirred solution of stannous chloride (2.19 g) in conclusion. HCl (4 ml), and the resulting mixture was stirred for 1 h. After filtering, the solution was reduced in volume until an inorganic precipitate formed. This was filtered off, and the filtrate was evaporated to dryness. The residual gum was crystallized from acetic acid to give crude 4-hydrazinophenyl propionamide hydrochloride (1.05 g).

A mixture of the above product (1.05 g) and 4-phthalimidocyclohexanone (1.18 g) in acetic acid (40 ml) was heated under reflux for 40 min. The solvent was removed in vacuo and the residue was partitioned between aqueous potassium carbonate solution and ethyl acetate. The organic phase was dried (MgSO$_4$) and evaporated to dryness, and the residue was chromatographed (SiO$_2$; CH$_2$Cl$_2$/MeOH) to give 3-phthalimido-6-carboxamidoethyl-1,2,3,4-tetrahydrocarbazole (0.70 g).

This product (0.70 g) was dissolved in methanol (50 ml), treated with hydrazine hydrate (1.0 ml), and heated under reflux for 30 min. The mixture was evaporated to dryness then partitioned between ethyl acetate and aqueous potassium carbonate solution. The organic phase was dried (MgSO$_4$) and evaporated to dryness, and the residue was dissolved in ethanol to dryness, and the residue was dissolved in ethanol and treated with oxalic acid (83 mg) in ethanol. A solid was formed, which was recrystallized from ethanol to give the title compound (110 mg), mp 232°–5° C.

Pharmaceutical formulations

Example A

A tablet for oral administration is prepared by combining

|  | Mg/Tablet |
|---|---|
| Compound of formula (I) | 100 |
| lactose | 153 |

-continued

|  | Mg/Tablet |
| --- | --- |
| starch | 33 |
| crospovidone | 12 |
| microcrystalline cellulose | 30 |
| magnesium stearate | 2 |
|  | 330 mg | into a 9 mm tablet.

Example B

An injection for parenteral administration is prepared from the following

|  | % w:w |
| --- | --- |
| Compound of formula (I) | 0,50% (w:v) |
| 1M citric acid | 30% (v:v) |
| sodium hydroxide (qs) | to pH 3.2 |
| water for injection BP | to 100 ml |

The compound of formula (I) is dissolved in the citric acid and the pH slowly adjusted to pH 3.2 with the sodium hydroxide solution. The solution is then made up to 100 ml with water, sterilised by filtration and sealed into appropriately sized ampoules and vials.

We claim:

1. A method of treatment of a condition wherein a 5-$HT_1$-like agonist is indicated, which comprises administering to a subject in need thereof an effective amount of a compound of general formula (I):

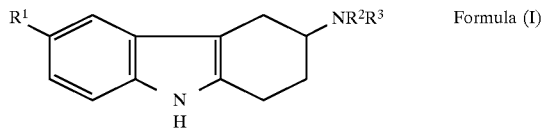

Formula (I)

wherein $R^1$ represents hydrogen, halogen, trifluoromethyl, nitro, hydroxy, $C_{1-6}$alkyl, $C_{1-6}$alkoxy, aryl$C_{1-6}$alkoxy, —$CO_2R^4$, —$(CH_2)_nCN$, —$(CH_2)_nCONR^5R^6$, —$(CH_2)_nSO_2NR^5R^6$, $C_{1-6}$alkanoylamino$(CH_2)_n$, or $C_{1-6}$alkylsulphonylamino$(CH_2)_n$;

$R^4$ represents hydrogen, $C_{1-6}$alkyl or aryl$C_{1-6}$alkyl;

$R^5$ and $R^6$ each independently represent hydrogen or $C_{1-6}$alkyl, or $R^5$ and $R^6$ together with the nitrogen atom to which they are attached form a 5 to 7-membered saturated heterocyclic ring, which may optionally contain a further heteroatom selected from oxygen, sulphur or nitrogen;

n represents 0, 1 or 2; and $R^2$ and $R^3$ each independently represent hydrogen, $C_{1-6}$alkyl or benzyl or together with the nitrogen atom to which they are attached form a pyrrolidino, piperidino or hexahydroazepino ring;

or a physiologically acceptable salt, solvate or hydrate thereof.

2. The method according to claim 1 wherein the condition is migraine.

3. The method according to claim 1 wherein in the compound of formula (I) $R^1$ represents halogen, $CF_3$, $C_{1-6}$alkoxy, —$(CH_2)_nCN$, —$(CH_2)_nCONR^5R^6$, —$(CH_2)_nSO_2RN^5R^6$ or $C_{1-6}$alkanoylamino, and $R^5$ and $R^6$ are as hereinbefore defined.

4. The method according to claim 1 wherein in the compound of formula (I) $R^1$ is a group —$(CH_2)_nCONR^5R^6$ wherein n is zero and $R^5$ and $R^6$ each independently represent hydrogen, methyl, ethyl or propyl; and $R^2$ and $R^3$ each independently represent hydrogen, methyl or ethyl.

5. The method according to claim 2 wherein in the compound of formula (I) $R^1$ is a group —$(CH_2)_nCONR^5R^6$ wherein n is zero and $R^5$ and $R^6$ each independently represent hydrogen, methyl, ethyl or propyl; and $R^2$ and $R^3$ each independently represent hydrogen, methyl or ethyl.

6. The method according to claim 4 wherein in the compound of formula (I) $R^5$ and $R^6$ each independently represent hydrogen or methyl.

7. The method according to claim 5 wherein in the compound of formula (I) $R^5$ and $R^6$ each independently represent hydrogen or methyl.

8. A compound of formula (IA):

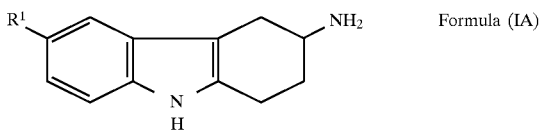

Formula (IA)

wherein $R^1$ represents nitro, —$CO_2R^4$, CN, —$(CH_2)_nCONR^5R^6$, —$(CH_2)_nSO_2NR^5R^6$, or $C_{1-6}$alkylsulphonylamino $(CH_2)_n$;

$R^4$ represents aryl$C_{1-6}$alkyl;

$R^5$ and $R^6$ each independently represent hydrogen or $C_{1-6}$alkyl, or $R^5$ and $R^6$ together with the nitrogen atom to which they are attached form a 5 to 7-membered saturated heterocyclic ring, which may optionally contain a further heteroatom selected from oxygen, sulphur or nitrogen; and n represents 0, 1 or 2;

or a physiologically acceptable salt, solvate or hydrate thereof.

9. A compound of formula (IA) according to claim 8 wherein $R^1$ represents —$(CH_2)_nCONR^5R^6$, wherein n represents 0 and $R^5$ and $R^6$ each independently represent hydrogen, methyl, ethyl or propyl.

10. A compound of formula (IA) according to claim 9 wherein $R^5$ and $R^6$ each independently represent hydrogen or methyl.

11. A compound of formula (I) according to claim 8, which is selected from:

3-Amino-6-cyano-1,2,3,4-tetrahydrocarbazole;

3-amino-6-(N-methylsulphonamidomethyl)-1,2,3,4-tetrahydrocarbazole;

3-amino-6-sulphonamido-1,2,3,4-tetrahydrocarbazole;

3-amino-6-nitro-1,2,3,4-tetrahydrocarbazole;

3-amino-6-(piperidin-1-ylcarbonyl)-1,2,3,4-tetrahydrocarbazole;

3-amino-6-(pyrrolidin-1-ylcarbonyl)-1,2,3,4-tetrahydrocarbazole;

3-amino-6-methanesulphonamido-1,2,3,4-tetrahydrocarbazole;

or a physiologically acceptable salt, solvate or hydrate thereof.

12. A compound of formula (I) according to claim 8, which is selected from:

3-amino-6-(N-methylcarboxamido)-1,2,3,4-tetrahydrocarbazole;

3-amino-6-(N,N-dimethylcarboxamido)-1,2,3,4-tetrahydrocarbazole;

3-amino-6-(N,N-diethylcarboxamido)-1,2,3,4-tetrahydrocarbazole;

or a physiologically acceptable salt, solvate or hydrate thereof.

13. A compound of formula (I) according to claim 8, which is selected from:

3-amino-6-carboxamidomethyl-1,2,3,4-tetrahydrocarbazole;

3-amino-6-(2-carboxamidoethyl)-1,2,3,4-tetrahydrocarbazole;

or a physiologically acceptable salt, solvate or hydrate thereof.

14. A compound of formula (I) according to claim 8, which is (+)-3-amino-6-carboxamido-1,2,3,4-tetrahydrocarbazole or a physiologically acceptable salt, solvate or hydrate thereof.

15. A compound of formula (I) according to claim 8, which is (−)-3-amino-6-carboxamido-1,2,3,4-tetrahydrocarbazole or a physiologically acceptable salt, solvate or hydrate thereof.

16. A compound of formula (I) according to claim 8 wherein the said physiologically acceptable salt is formed from hydrochloric, sulphuric, phosphoric, succinic, maleic, acetic or fumaric acid.

17. A pharmaceutical composition comprising a compound of formula (I) according to claim 8, or a physiologically acceptable salt, solvate or hydrate thereof and a physiologically acceptable carrier.

* * * * *

UNITED STATES PATENT AND TRADEMARK OFFICE
CERTIFICATE OF CORRECTION

PATENT NO. : 5,827,871
DATED : October 27, 1998
INVENTOR(S) : King et al.

It is certified that error appears in the above-identified patent and that said Letters Patent is hereby corrected as shown below:

The filing date of May 17, 1995 is incorrect and should be May 15, 1995

Signed and Sealed this

Eighth Day of June, 1999

Attest:

Q. TODD DICKINSON

*Attesting Officer*     *Acting Commissioner of Patents and Trademarks*

Disclaimer

5,827,871 — Francis David King; Laramie Mary Gaster, both of Harlow; Alberto Julio Kaumann, Trumpington; Rodney Christopher Young, Hertford, all of England. MEDICAMENTS 1,2,3,4-TETRAHYDROCABAZOLES AND 5-HT1 AGONIST USE THEREOF. Patented dated October 27, 1998. Disclaimer filed October 30, 2013, by the assignee, Endo Pharmaceuticals Inc.

The term of this patent shall not extend beyond the expiration date of Pat. No. 5,637,611 and 5,464,864.

*(Official Gazette, December 31, 2013)*